(12) United States Patent
Wood et al.

(10) Patent No.: US 6,248,875 B1
(45) Date of Patent: Jun. 19, 2001

(54) NEURONAL MORT1 ISOFORMS

(75) Inventors: Andrew T. Wood; Brendan William Bingham; Kathleen H. Young, all of Newtown, PA (US); Camelia Birsan, Plainsboro, NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/064,414

(22) Filed: Apr. 22, 1998

Related U.S. Application Data (60) Provisional application No. 60/044,835, filed on Apr. 25, 1997, now abandoned.

(51) Int. Cl.[7] .................................................. C12N 15/12
(52) U.S. Cl. ..................... 536/23.5; 435/320.1; 435/69.1
(58) Field of Search ........................ 536/23.5; 435/69.1, 435/320.1

(56) References Cited

FOREIGN PATENT DOCUMENTS

| WO 95/34646 | 12/1995 | (WO) . |
|---|---|---|
| 9618641 | * 6/1996 | (WO) . |
| WO 96/25941 | 8/1996 | (WO) . |
| WO 96/31603 | 10/1996 | (WO) . |
| WO 97/18313 | 5/1997 | (WO) . |

OTHER PUBLICATIONS

Boldin et al., "A Novel Protein that Interacts with the Death Domain of Fas/APO–1 Contains a Sequence of Motif Related to the Death Domain," *J. Biol. Chem.*, 270(14): 7795–7798 (1995).

Chinnaiyan et al., "FADD, a Novel Death Domain–Containing Protein, Interacts with the Death Domain of Fas and Initiates Apoptosis," 81: 505–512 (1995).

Boldin et al., "Involvement of MACH, a Novel MORT1/FADD–Interacting Protease, in Fas/APO–1 and TNF Receptor–Induced Cell Death," *Cell*, 85: 803–815 (1996).

Fisher et al., "Dominant Interfering Fas Gene Mutations Impair Apoptosis in a Human Autoimmune Lymphoproliferative Syndrome," *Cell*, 81: 935–946 (1995).

P.A. Henkart, "ICE Family Proteases: Mediators of All Apoptotic Cell Death?," *Immunity*, 4: 195–201 (1996).

Peter K.M. Kim et al., "Genomic Structure and Mapping of Human FADD, an Intracellular Mediator of Lymphocyte Apoptosis[1,2]," *J. Immunology*, 157:5461–5466.

Kischkel et al., "Cytotoxicity–Dependent APO–1 (Fas/CD95)–Associated Proteins Form a Death–Inducing Signaling Complex (DISC) with the Receptor," *EMBO J.*, 14(22): 5579–5588 (1995).

S. Nagata, "Fas and Fas Ligand: A Death Factor and its Receptor," *Adv. Immunol.*, 57: 129–144 (1994).

Rieux–Laucat et al., "Mutations in Fas Associated with Human Lumphoproliferative Syndrome and Autoimmunity," *Science*, 268: 1347–1349 (1995).

C.B. Thompson, "Apoptosis in the Pathogenesis and Treatment of Disease," *Science*, 267: 1456–1462 (1995).

Wanker et al., "HIP–I: a Huntingtin Interacting Protein Isolated by the Yeast Two–Hybrid System," *Hum. Mol. Genet.*, 6(3): 487–495 (1997).

Bingham et al., "Human Neuronal Sequence Variants of the Mediator of Apoptosis, MORT1," *Society for Neuroscience Abstracts*, 23(1–2): 896 (1997).

* cited by examiner

*Primary Examiner*—Karen Cochrane Carlson
*Assistant Examiner*—Gabriele E. Bugaisky
(74) *Attorney, Agent, or Firm*—Barbara A. Gyure

(57) ABSTRACT

A MORT1 gene initially cloned from HeLa cells and identified as a member of the receptor mediated apoptotic pathway, is expressed in the human neuronal cell line, NTERA2. Isolation of the MORT1 from this cell line revealed a transcript isoform that differed from the known MORT1 sequence by a deletion of 21 base pairs (bp 172–192 of the coding sequence). Cloning of MORT1 from adult human brain revealed two isoforms, one similarly deleted for bp 172–192, the other with a basepair substitution, A for G at position 173. Assessment of MORT1 function in a yeast two hybrid system indicates that the deleted and intact forms of MORT1 differ in their capacity to interact with other members of the apoptotic pathway.

3 Claims, 2 Drawing Sheets

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 606 base pairs
      (B) TYPE: nucleic acid
      (C) STRANDEDNESS: single
      (D) TOPOLOGY: linear    (ii) MOLECULE TYPE: cDNA    (ix) FEATURE:
      (A) NAME/KEY: CDS
      (B) LOCATION: 1..606

(xi) SEQUENCE DESCRIPTION: SEQ ID NO: 1:

```
ATG GAC CCG TTC CTG GTG CTG CTG CAC TCG GTG TCG TCC AGC CTG TCG      48
Met Asp Pro Phe Leu Val Leu Leu His Ser Val Ser Ser Leu Ser
 1               5                  10                  15

AGC AGC GAG CTC ACC GAG CTC AAG TTC CTA TGC CTC GGG CGC GTG GGC      96
Ser Ser Glu Leu Thr Glu Leu Lys Phe Leu Cys Leu Gly Arg Val Gly
```

|  |  |  |  |  |  |  |  |  |  |  |  |  |  |  |  |
|---|---|---|---|---|---|---|---|---|---|---|---|---|---|---|---|
|  |  |  | 20 |  |  |  |  | 25 |  |  |  |  | 30 |  |  |
| AAG | CGC | AAG | CTG | GAG | CGC | GTG | CAG | AGC | GGC | CTA | GAC | CTC | TTC | TCC | ATG |
| Lys | Arg | Lys | Leu | Glu | Arg | Val | Gln | Ser | Gly | Leu | Asp | Leu | Phe | Ser | Met |
|  |  | 35 |  |  |  |  | 40 |  |  |  |  | 45 |  |  |  |

144

CTG CTG GAG CAG AAC GAC CTG GAG CCC GAG CTG CTC GCC TCC CTG CGG    192
Leu Leu Glu Gln Asn Asp Leu Glu Pro Glu Leu Leu Ala Ser Leu Arg
         50                  55                  60

CGC CAC GAC CTG CTG CGG CGC GTC GAC GAC TTC GAG GCG GGG GCG GCG    240
Arg His Asp Leu Leu Arg Arg Val Asp Asp Phe Glu Ala Gly Ala Ala
65                   70                  75                  80

GCC GGG GCC GCG CCT GGG GAA GAA GAC CTG TGT GCA GCA TTT AAC GTC    288
Ala Gly Ala Ala Pro Gly Glu Glu Asp Leu Cys Ala Ala Phe Asn Val
                 85                  90                  95

ATA TGT GAT AAT GTG GGG AAA GAT TGG AGA AGG CTG GCT CGT CAG CTC    336
Ile Cys Asp Asn Val Gly Lys Asp Trp Arg Arg Leu Ala Arg Gln Leu
             100                 105                 110

AAA GTC TCA GAC ACC AAG ATC GAC AGC ATC GAG GAC AGA TAC CCC CGC    384
Lys Val Ser Asp Thr Lys Ile Asp Ser Ile Glu Asp Arg Tyr Pro Arg
         115                 120                 125

AAC CTG ACA GAG CGT GTG CGG GAG TCA CTG AGA ATC TGG AAG AAC ACA    432
Asn Leu Thr Glu Arg Val Arg Glu Ser Leu Arg Ile Trp Lys Asn Thr
     130                 135                 140

GAG AAG GAG AAC GCA ACA GTG GCC CAC CTG GTG GGG GCT CTC AGG TCC    480
Glu Lys Glu Asn Ala Thr Val Ala His Leu Val Gly Ala Leu Arg Ser
145                 150                 155                 160

TGC CAG ATG AAC CTG GTG GCT GAC CTG GTA CAA GGG GTT CAG CAG GCC    528
Cys Gln Met Asn Leu Val Ala Asp Leu Val Gln Gly Val Gln Gln Ala
                 165                 170                 175

CGT GAC CTC CAG AAC AGG AGT GGG GCC ATG TCC CCG ATG TCA TGG AAC    576
Arg Asp Leu Gln Asn Arg Ser Gly Ala Met Ser Pro Met Ser Trp Asn
             180                 185                 190

TCA GAC GCA TCT ACC TCC GAA GCG TCC TGA                            606
Ser Asp Ala Ser Thr Ser Glu Ala Ser *
         195                 200

(2) INFORMATION FOR SEQ ID NO: 2:

(i) SEQUENCE CHARACTERISTICS:
        (A) LENGTH: 201 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Pro Phe Leu Val Leu Leu His Ser Val Ser Ser Ser Leu Ser
1               5                   10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
        35                  40                  45

Leu Leu Glu Gln Asn Asp Leu Pro Glu Leu Leu Ala Ser Leu Arg
    50                  55                  60

Arg His Asp Leu Leu Arg Arg Val Asp Asp Phe Glu Ala Gly Ala Ala
65                  70                  75                  80

Ala Gly Ala Ala Pro Gly Glu Glu Asp Leu Cys Ala Ala Phe Asn Val
                85                  90                  95

Ile Cys Asp Asn Val Gly Lys Asp Trp Arg Arg Leu Ala Arg Gln Leu
            100                 105                 110

```
Lys Val Ser Asp Thr Lys Ile Asp Ser Ile Glu Asp Arg Tyr Pro Arg
        115                 120                 125

Asn Leu Thr Glu Arg Val Arg Glu Ser Leu Arg Ile Trp Lys Asn Thr
        130                 135                 140

Glu Lys Glu Asn Ala Thr Val Ala His Leu Val Gly Ala Leu Arg Ser
145                 150                 155                 160

Cys Gln Met Asn Leu Val Ala Asp Leu Val Gln Gly Val Gln Gln Ala
                165                 170                 175

Arg Asp Leu Gln Asn Arg Ser Gly Ala Met Ser Pro Met Ser Trp Asn
            180                 185                 190

Ser Asp Ala Ser Thr Ser Glu Ala Ser
        195                 200

(2) INFORMATION FOR SEQ ID NO: 3:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..606

(xi) SEQUENCE DESCRIPTION: SEQ ID NO: 3:

ATG GAC CCG TTC CTG GTG CTG CTG CAC TCG GTG TCG TCC AGC CTG TCG     48
Met Asp Pro Phe Leu Val Leu Leu His Ser Val Ser Ser Ser Leu Ser
 1               5                  10                  15

AGC AGC GAG CTG ACC GAG CTC AAG TTC CTA TGC CTC GGG CGC GTG GGC     96
Ser Ser Glu Leu Thr Glu Leu Lys Phe Leu Cys Leu Gly Arg Val Gly
                20                  25                  30

AAG CGC AAG CTG GAG CGC GTG CAG AGC GGC CTA GAC CTC TTC TCC ATG    144
Lys Arg Lys Leu Glu Arg Val Gln Ser Gly Leu Asp Leu Phe Ser Met
            35                  40                  45

CTG CTG GAG CAG AAC GAC CTG GAG CCC GAG CTG CTC GCC TCC CTG CGG    192
Leu Leu Glu Gln Asn Asp Leu Glu Pro Glu Leu Leu Ala Ser Leu Arg
        50                  55                  60

CGC CAC GAC CTG CTG CGG CGC GTC GAC GAC TTC GAG GCG GGG GCG GCA    240
Arg His Asp Leu Leu Arg Arg Val Asp Asp Phe Glu Ala Gly Ala Ala
 65                  70                  75                  80

GCC GGG GCC GCG CCT GGG GAA GAA GAC CTG TGT GCA GCA TTT AAC GTC    288
Ala Gly Ala Ala Pro Gly Glu Glu Asp Leu Cys Ala Ala Phe Asn Val
                85                  90                  95

ATA TGT GAT AAT GTG GGG AAA GAT TGG AGA AGG CTG GCT CGT CAG CTC    336
Ile Cys Asp Asn Val Gly Lys Asp Trp Arg Arg Leu Ala Arg Gln Leu
            100                 105                 110

AAA GTC TCA GAC ACC AAG ATC GAC AGC ATC GAG GAC AGA TAC CCC CGC    384
Lys Val Ser Asp Thr Lys Ile Asp Ser Ile Glu Asp Arg Tyr Pro Arg
        115                 120                 125

AAC CTG ACA GAG CGT GTG CGG GAG TCA CTG AGA ATC TGG AAG AAC ACA    432
Asn Leu Thr Glu Arg Val Arg Glu Ser Leu Arg Ile Trp Lys Asn Thr
        130                 135                 140

GAG AAG GAG AAC GCA ACA GTG GCC CAC CTG GTG GGG GCT CTC AGG TCC    480
Glu Lys Glu Asn Ala Thr Val Ala His Leu Val Gly Ala Leu Arg Ser
145                 150                 155                 160

TGC CAG ATG AAC CTG GCG GCT GAC CTG GTA CAA GAG GTT CAG CAG GCC    528
Cys Gln Met Asn Leu Ala Ala Asp Leu Val Gln Glu Val Gln Gln Ala
                165                 170                 175
```

```
CGT GAC CTC CAG AAC AGG AGT GGG GCC ATG TCC CCG ATG TCA TGG AAC      576
Arg Asp Leu Gln Asn Arg Ser Gly Ala Met Ser Pro Met Ser Trp Asn
            180                 185                 190

TCA GAC GCA TCT ACC TCC GAA GCG TCC TGA                              606
Ser Asp Ala Ser Thr Ser Glu Ala Ser  *
        195                 200
```

(2) INFORMATION FOR SEQ ID NO: 4:

(i) SEQUENCE CHARACTERISTICS:
        (A) LENGTH: 201 amino acids
        (B) TYPE: amino acid
        (D) TOPOLOGY: linear     (ii) MOLECULE TYPE: protein     (xi) SEQUENCE DESCRIPTION: SEQ ID NO: 4:

```
Met Asp Pro Phe Leu Val Leu Leu His Ser Val Ser Ser Ser Leu Ser
 1               5                  10                  15

Ser Ser Glu Leu Thr Glu Leu Lys Phe Leu Cys Leu Gly Arg Val Gly
                20                  25                  30

Lys Arg Lys Leu Glu Arg Val Gln Ser Gly Leu Asp Leu Phe Ser Met
            35                  40                  45

Leu Leu Glu Gln Asn Asp Leu Glu Pro Glu Leu Leu Ala Ser Leu Arg
    50                  55                  60

Arg His Asp Leu Leu Arg Arg Val Asp Asp Phe Glu Ala Gly Ala Ala
65                  70                  75                  80

Ala Gly Ala Ala Pro Gly Glu Glu Asp Leu Cys Ala Ala Phe Asn Val
                85                  90                  95

Ile Cys Asp Asn Val Gly Lys Asp Trp Arg Arg Leu Ala Arg Gln Leu
                100                 105                 110

Lys Val Ser Asp Thr Lys Ile Asp Ser Ile Glu Asp Arg Tyr Pro Arg
            115                 120                 125

Asn Leu Thr Glu Arg Val Arg Glu Ser Leu Arg Ile Trp Lys Asn Thr
    130                 135                 140

Glu Lys Glu Asn Ala Thr Val Ala His Leu Val Gly Ala Leu Arg Ser
145                 150                 155                 160

Cys Gln Met Asn Leu Ala Ala Asp Leu Val Gln Glu Val Gln Gln Ala
                165                 170                 175

Arg Asp Leu Gln Asn Arg Ser Gly Ala Met Ser Pro Met Ser Trp Asn
            180                 185                 190

Ser Asp Ala Ser Thr Ser Glu Ala Ser
        195                 200
```

(2) INFORMATION FOR SEQ ID NO: 5:

(i) SEQUENCE CHARACTERISTICS:
        (A) LENGTH: 627 base pairs
        (B) TYPE: nucleic acid
        (C) STRANDEDNESS: single
        (D) TOPOLOGY: linear     (ii) MOLECULE TYPE: cDNA     (ix) FEATURE:
        (A) NAME/KEY: CDS
        (B) LOCATION: 1..627

(xi) SEQUENCE DESCRIPTION: SEQ ID NO: 5:

```
ATG GAC CCG TTC CTG GTG CTG CTG CAC TCG GTG TCG TCC AGC CTG TCG       48
Met Asp Pro Phe Leu Val Leu Leu His Ser Val Ser Ser Ser Leu Ser
 1               5                  10                  15
```

```
AGC AGC GAG CTG ACC GAG CTC AAG TTC CTA TGC CTC GGG CGC GTG GGC        96
Ser Ser Glu Leu Thr Glu Leu Lys Phe Leu Cys Leu Gly Arg Val Gly
            20                  25                  30

AAG CGC AAG CTG GAG CGC GTG CAG AGC GGC CTA GAC CTC TTC TCC ATG       144
Lys Arg Lys Leu Glu Arg Val Gln Ser Gly Leu Asp Leu Phe Ser Met
        35                  40                  45

CTG CTG GAG CAG AAC GAC CTG GAG CCC GAG CAC ACC GAG CTC CTG CGC       192
Leu Leu Glu Gln Asn Asp Leu Glu Pro Glu His Thr Glu Leu Leu Arg
    50                  55                  60

GAG CTG CTC GCC TCC CTG CGG CGC CAC GAC CTG CTG CGG CGC GTC GAC       240
Glu Leu Leu Ala Ser Leu Arg Arg His Asp Leu Leu Arg Arg Val Asp
65                  70                  75                  80

GAC TTC GAG GCG GGG GCG GCA GCC GGG GCC GCG CCT GGG GAA GAA GAC       288
Asp Phe Glu Ala Gly Ala Ala Ala Gly Ala Ala Pro Gly Glu Glu Asp
                85                  90                  95

CTG TGT GCA GCA TTT AAC GTC ATA TGT GAT AAT GTG GGG AAA GAT TGG       336
Leu Cys Ala Ala Phe Asn Val Ile Cys Asp Asn Val Gly Lys Asp Trp
            100                 105                 110

AGA AGG CTG GCT CGT CAG CTC AAA GTC TCA GAC ACC AAG ATC GAC AGC       384
Arg Arg Leu Ala Arg Gln Leu Lys Val Ser Asp Thr Lys Ile Asp Ser
        115                 120                 125

ATC GAG GAC AGA TAC CCC CGC AAC CTG ACA GAG CGT GTG CGG GAG TCA       432
Ile Glu Asp Arg Tyr Pro Arg Asn Leu Thr Glu Arg Val Arg Glu Ser
    130                 135                 140

CTG AGA ATC TGG AAG AAC ACA GAG AAG GAG AAC GCA ACA GTG GCC CAC       480
Leu Arg Ile Trp Lys Asn Thr Glu Lys Glu Asn Ala Thr Val Ala His
145                 150                 155                 160

CTG GTG GGG GCT CTC AGG TCC TGC CAG ATG AAC CTG GCG GCT GAC CTG       528
Leu Val Gly Ala Leu Arg Ser Cys Gln Met Asn Leu Ala Ala Asp Leu
                165                 170                 175

GTA CAA GAG GTT CAG CAG GCC CGT GAC CTC CAG AAC AGG AGT GGG GCC       576
Val Gln Glu Val Gln Gln Ala Arg Asp Leu Gln Asn Arg Ser Gly Ala
            180                 185                 190

ATG TCC CCG ATG TCA TGG AAC TCA GAC GCA TCT ACC TCC GAA GCG TCC       624
Met Ser Pro Met Ser Trp Asn Ser Asp Ala Ser Thr Ser Glu Ala Ser
        195                 200                 205

TGA                                                                   627
 *
```

(2) INFORMATION FOR SEQ ID NO: 6:

(i) SEQUENCE CHARACTERISTICS:
        (A) LENGTH: 208 amino acids
        (B) TYPE: amino acid
        (D) TOPOLOGY: linear     (ii) MOLECULE TYPE: protein     (xi) SEQUENCE DESCRIPTION: SEQ ID NO: 6:

```
Met Asp Pro Phe Leu Val Leu Leu His Ser Val Ser Ser Ser Leu Ser
1               5                   10                  15

Ser Ser Glu Leu Thr Glu Leu Lys Phe Leu Cys Leu Gly Arg Val Gly
            20                  25                  30

Lys Arg Lys Leu Glu Arg Val Gln Ser Gly Leu Asp Leu Phe Ser Met
        35                  40                  45

Leu Leu Glu Gln Asn Asp Leu Glu Pro Glu His Thr Glu Leu Leu Arg
    50                  55                  60

Glu Leu Leu Ala Ser Leu Arg Arg His Asp Leu Leu Arg Arg Val Asp
65                  70                  75                  80
```

```
Asp Phe Glu Ala Gly Ala Ala Ala Gly Ala Ala Pro Gly Glu Glu Asp
                85                  90                  95

Leu Cys Ala Ala Phe Asn Val Ile Cys Asp Asn Val Gly Lys Asp Trp
            100                 105                 110

Arg Arg Leu Ala Arg Gln Leu Lys Val Ser Asp Thr Lys Ile Asp Ser
        115                 120                 125

Ile Glu Asp Arg Tyr Pro Arg Asn Leu Thr Glu Arg Val Arg Glu Ser
    130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Ala Ala Asp Leu
                165                 170                 175

Val Gln Glu Val Gln Gln Ala Arg Asp Leu Gln Asn Arg Ser Gly Ala
            180                 185                 190

Met Ser Pro Met Ser Trp Asn Ser Asp Ala Ser Thr Ser Glu Ala Ser
            195                 200                 205
```

NEURONAL MORT1 ISOFORMS

CROSS REFERENCE TO RELATED APPLICATIONS

This application is a continuation of provisional application serial No. 60-044,835 filed Apr. 25, 1997 (now abandoned).

FIELD OF THE INVENTION

The present invention relates to human intracellular death-domain-containing apoptosis signaling proteins. In particular, the present invention relates to novel human neuronal MORT1 isoforms.

BACKGROUND

Apoptosis, or programmed cell death in multicellular organisms, is one of the fundamental means by which a cell can respond to environmental changes. One of the best studied mammalian apoptosis systems involves Fas (also designated APO-1 and CD95), a type I membrane receptor that, when crosslinked by its cognate ligand, induces apoptosis in a wide variety of cells (for review, see Nagata, 1994). The extracellular interaction of Fas ligand with the cell membrane-spanning Fas receptor activates an intracellular signal transduction cascade finally activating proteases in the IL-1β-converting enzyme (ICE) family (Henkart, 1996). Transduction of an apoptosis signal depends on interaction between the intracellular "death domain" of Fas with a cytoplasmic 23-kDa protein, MORT1 [(Boldin, et al., 1995), also termed FADD (Chinnaiyan, et al., 1995)]. The events leading from the production of an activated Fas trimer complex to cell destruction mediated by ICE-like proteases are yet to be determined, but recruitment of two MORT1/FADD molecules into a death-inducing signaling complex with the death domain of Fas appears to be a necessary step (Kischkel, et al., 1995). The end result of this pathway is cell death by a distinctive mechanism characterized by nuclear and cytoplasmic condensation and DNA fragmentation.

The human MORT1/FADD gene spans approximately 3.6 kb and contains two exons (286 and 341 bp) separated by a 2.0-kb intron. MORT1/FADD was mapped to chromosome 11q13.3 by the independent techniques of PCR screening of somatic cell hybrid mapping panels and fluorescence in situ hybridization (Kim, et al., 1996). Knowledge of the chromosomal location and gene structure of MORT1/FADD will assist efforts to determine its involvement in genetic disorders of apoptosis. Defects in apoptosis due to mutations in the Fas receptor have been described (Fisher, et al., 1995; Rieux-Laucat, et al., 1995) in patients with a rare autoimmune lymphoproliferative syndrome (ALPS) including non-malignant lymphadenopathy, hepatosplenomegaly, and expanded populations of CD3$^+$CD4$^-$CD8$^-$ lymphocytes. However, the existence of some patients with clinical findings of ALPS, but no Fas mutation, suggests that defects in other proteins in the Fas pathway may also produce ALPS. The functional involvement of MORT1/FADD in the Fas pathway makes it a candidate for mutation analysis in ALPS.

Localization of MORT1/FADD to 11q13.3 also makes it a candidate for human diseases associated with this part of the genome. IDDM4, a predisposing locus for familial insulin-dependent diabetes mellitus (IDDM) has been mapped to this region by linkage studies (Cordell, et al., 1995; Davies, et al., 1994; Hashimoto, et al., 1995). The pathogenesis of IDDM may involve autoimmune T lymphocyte-mediated destruction of pancreatic β islet cells that produce insulin (Tisch and McDevitt, 1996). MORT1/FADD's chromosomal location, coupled with its known role in lymphocyte apoptosis, makes it a candidate for mutational analysis in patients with IDDM4-linked familial diabetes.

In addition, the 11q13 region is amplified in several human malignancies, including carcinoma of the breast, bladder, esophagus, head and neck, and lung (Schuuring, 1995; Szepetowski, et al., 1995). Amplification of this region has been associated with poor prognosis in patients with operable breast cancer (Schuuring, et al., 1992). The mapping of MORT1/FADD to the amplicon of the breast cancer cell line MDA-MB-134-VI (Lafage, et al., 1992) raises the possibility of its involvement in tumor growth. Future linkage and mutation analysis of MORT1/FADD in other diseases may support the hypothesis that disregulation of cell death is a fundamental mechanism for the pathogenesis of human disease (Thompson, 1995).

A single gene can encode more than one mRNA transcript by transcriptional processing events such as use of alternative promoters, alternative splicing, and alternative polyadenylation (Farrow, 1997; Lewin, 1994). The resulting variant transcript isoforms may differ in stability, translatability, or protein sequence encoded, each of which may impact upon the function of the encoded protein. Transcript variants resulting from alternative RNA processing can be tissue-specific, developmentally regulated, endocrine regulated, or can appear in response to specific exogenous cues. In addition, transcript variants of a gene can result from differences in genomic sequence (among individuals or among cell lines).

To date, only one transcript isoform has been reported for the MORT1/FADD gene (Boldin, et al., 1995; Chinnaiyan, et al., 1995). This invention describes the identification of two new isoforms of MORT1.

SUMMARY OF THE INVENTION

The present invention is based on the discovery of novel transcript isoforms of the human neuronal MORT1 gene. The transcript isoforms and the proteins encoded by them are useful as screening agents in the diagnosis of CNS diseases and in the discovery of CNS-specific anti-apoptotic compounds. The DNA, RNA, and proteins encoded by them are useful in a "gene therapy" scenario, either as in vivo therapeutic agents in humans, or as experimental tools in manipulating neuronal apoptosis in cell culture and animal model systems.

Accordingly, in one embodiment, the invention is directed to a neuronal protein encoded by an MORT1 gene, wherein the gene is isolated from NTERA2 or adult human brain tissue. The cDNA encoding the neuronal protein differs from the known MORT1 gene by the deletion of 21 base pairs and by base pair substitutions.

DETAILED DESCRIPTION OF THE INVENTION

The practice of the present invention will employ, unless otherwise indicated, conventional techniques of molecular biology, microbiology, recombinant DNA technology, and yeast biology and genetics, which are within the skill of the art. Such techniques are explained fully in the literature (e. g., Ausubel, et al., 1993; Coico, 1994; Freshney, 1987; Glover, 1985; Griffin and Griffin, 1994; Hanes and Higgins, 1984; Perbal, 1988; Rose et al., 1990; Sambrook, et al., 1989).

All patents, patent applications and publications cited herein, whether supra or infra, are hereby incorporated by reference in their entirety.

In describing the present invention, the following terms will be employed, and are intended to be defined as indicated below. By "MORT1 transcript isoform" is meant a nucleic acid molecule, including DNA, RNA, mRNA, cDNA derived from the mRNA, or even synthetic DNA, which is derived either directly or indirectly from a MORT1 genomic sequence. As used herein, the term specifically excludes the transcript described in Chinnaiyan, et al. (1995), Boldin, et al. (1995), and Genbank deposit x84709, and as Genbank x84709 MORT1. The term MORT1Δ21 denotes a cDNA isoform isolated from NTERA2 cells (SEQ. ID NO. 1) or adult human brain (SEQ. ID NO. 3) that has a specific 21 base pair deletion (bp 172–192 of the coding sequence) as compared to the published MORT1. The term MORT1G173A (SEQ. ID NO. 5) denotes a cDNA isoform isolated from human brain that has a nucleotide substitution (A for G) at bp position 173 of the MORT1 coding sequence.

Herein the A of the MORT1 translational initiation codon is designated position 1, and corresponds to bp 145 of Genbank sequence x84709.

The above terms (MORT1 transcript isoform, MORT1Δ21, MORT1G173A) encompass the genomic MORT1 sequence encoding them, including introns and exons. Alternatively, a transcript isoform can include transcripts of the genomic sequences which lack one or more introns or exons, or transcripts which incorporate noncoding or coding sequences different from those found in the full-length, wild-type genomic sequence. Transcript isoforms may arise by any of a number of naturally occurring processes, including but not limited to mutation, alternative initiation, alternative splicing, and alternative polyadenylation, each of which may affect the primary structure or some other aspect of the function of the encoded protein. The protein product of a transcript isoform may contain amino acids which differ from the wild-type protein due to insertion, deletion, or frameshifting of coding nucleotides. For example, the NTERA2 and the adult human brain isoforms of MORT1 are depicted in SEQ. ID NOS. 1 and 3.

The cDNA encoding intact MORT1 was generated using standard PCR techniques (Finney, 1993; Griffin and Griffin, 1994). HeLa cell cDNA prepared by standard reverse transcriptase/PCR was the source of DNA template. Additionally, MORT1 cDNA was generated using a human placental cDNA library as the template source. In each case, a MORT1 fragment was amplified by PCR, cloned and sequenced. DNA sequences obtained from placental and HeLa tissue were compared with the MORT1 sequence in Genbank deposit x84709.

The existence of a human neuronal MORT1 transcript was determined by RT/PCR. Human neuronal NTERA2 cells were grown under conditions to promote terminal differentiation to the neuronal phenotype and induced to undergo apoptosis by incubation with staurosporine. RNA extracted from these cells was subjected to RT/PCR using MORT1-specific primers. The resulting MORT1 fragment was cloned and its sequence compared to the MORT1 sequence in Genbank deposit x84709.

MORT1 was also cloned from fetal and adult human brain cDNA libraries by PCR. MORT1 fragments were amplified, cloned, and their sequence compared to the MORT1 sequence in Genbank deposit x84709. In summary, the MORT1 clones deriving from HeLa cells, the human placental library, and fetal human brain matched the Genbank MORT1 sequence. MORT1 clones from NTERA2 cells and three of five clones derived from human adult brain were deleted for bp 172–192 of the MORT1 coding sequence. The other two of the five clones derived from human adult brain had a single base pair substitution (G173A) relative to the Genbank MORT1 sequence. The 21 bp deletion and the G173A substitution both generate a Glu-Pro-Glu amino acid sequence at positions 56–58 of the protein sequence, versus the corresponding Glu-Pro-Gly sequence of the wild-type protein. In addition, the human neuronal MORT1 isoforms include some other basepair substitutions relative to Genbank sequence, as depicted in SEQ. ID NO. 1 and 3.

Human neuronal MORT1 transcript isoforms are also cloned from human cDNA phage libraries by probing with a radiolabelled MORT1 probe using published DNA hybridization methods (Ausubel et al., 1993; Sambrook, et al., 1989). Many human brain sub-region libraries are commercially available (Clontech; Stratagene) for screening. For tissues or neuronal cell lines for which no commercially available library exists, custom synthesis of a cDNA library is performed from poly(A)+RNA (service available from Clontech). Total RNA and poly(A) selection are performed according to published methods (Glover, 1985; Sambrook, et al., 1989).

Human MORT1 genomic sequence is cloned using standard PCR techniques (Griffin and Griffin, 1994) from human genomic DNA prepared by standard methods (Glover, 1985; Sambrook, et al., 1989).

The relative abundance of neuronal MORT1 transcript isoforms within a given tissue or cell line is assessed by RNase protection and S1 nuclease mapping, performed according to published methods (Ausubel, et al., 1993; Berk and Sharp, 1977; Lee and Costlow, 1987).

Specifically, oligonucleotide probes are designed to distinguish the 21 nucleotide difference between the deleted and intact MORT1 isoforms.

A yeast two-hybrid system as described in Young and Ozenberger, WO 95/34646 published Dec. 21, 1995, the whole of which is incorporated herein, was used to functionally characterize the ability of the MORT1 transcript isoforms to interact with MACHα1 C360S, a protein component of the cytoplasmic apparatus of the Fas/APO1 and TNF receptors. Expression vectors were constructed by fusing the GAL4 DNA-binding domain to the MORT1 transcript isoforms. A second expression vector was constructed by fusing the GAL4 Activation domain to MACHα1 C360S. To determine the ability of the MORT1 transcript isoforms to interact with MACHα1 C360S, yeast strains were generated expressing a single MORT1 transcript isoform with MACHα1 C360S, or a single recombinant plasmid encoding a fusion protein with its companion vector containing unrelated heterologous DNA. Strains were tested for productive protein-protein interaction via reporter gene activity and a change in the yeast cell phenotype.

These data suggest that the MORTΔ21 isoform fusion protein is impaired in its ability to functionally interact with MACHα1 C360S fusion protein. The yeast strains expressing MORTΔ21 with MACHα1 C360S demonstrated decreased histidine prototrophy, and decreased cell growth, as well as decreased sensitivity to cycloheximide and increased cell growth. These were observed in comparison to the growth characteristics of yeast strain expressing the fusion proteins for MORT1 with MACHα1 C360S, or MORTG173A with MACHα1 C360S.

The subject nucleic acids find a wide variety of applications including use as translatable transcripts, hybridization probes, PCR primers, therapeutic nucleic acids, etc.; use in detecting the presence of genes and gene transcripts involved in apoptosis, in detecting or amplifying nucleic acids encoding additional MORT1 homologs and structural analogs, and in gene therapy applications. The gene products encoded by these transcripts have utility in serving as target proteins in the development of therapeutics for the manipulation of the apoptotic pathway.

The following experiments and examples are offered by way of illustration and not by way of limitation.

EXAMPLES

Example 1

Cloning of MORT1 from HeLa Cells and from a Human Placental cDNA Library.

As a control, the intact MORT1 gene was cloned as described in Boldin, et al., (1995). Oligonucleotides were prepared on an ABI oligosynthesizer, designed according to the published cDNA sequence of human MORT1 (Genbank x84709). A 25 base 5' sense oligonucleotide containing a NcoI site and the start codon ("5' MORT1," 5'-ACC CCG CCA TGG ACC CGT TCC TGG T-3', corresponding to bases −8 to +17), and a 24 base 3' antisense oligonucleotide spanning the stop codon ("3' MORT1," 5'-ACG GGC CCA TCA GGA CGC TTC GGA-3', complementary to bases 636 to 613 of the MORT1 coding sequence), were synthesized. The cDNA encoding intact MORT1 was generated using standard PCR techniques (Finney, 1993). Thermal cycling of these reactions was performed under the regime, 1 min at 95C, then 30 cycles (40 sec at 95C, 1 min at 60C, 1 min at 72C), and 10 min at 72C, using the oligonucleotides "5' MORT1" and "3' MORT1. " HeLa cell cDNA and a human placental (matchmaker) cDNA library (Clontech) served as the DNA templates. In each case, a 640 bp fragment was obtained by PCR and subsequently ligated into the cloning vector pCR II (Invitrogen). The HeLa and placental MORT1 cDNA sequences matched the coding sequence of the published MORT1 sequence (Genbank deposit x84709).

Example 2

Cloning of a Neuronal MORT1 from NTERA2 Cells by RT/PCR Using a Gene-specific RT Primer In order to investigate whether MORT1 was present in neuronal cells, NTERA-2 cells, which originate from a human teratocarcinoma and represent a late embryonic human neuronal phenotype, were investigated for the presence of MORT1. NTERA2 cells (Stratagene) were grown under conditions to promote terminal differentiation to the neuronal phenotype, including long-term incubation in retinoic acid (Andrews, 1984). Eighteen hours prior to RNA extraction, staurosporine (Calbiochem) was added to the cell culture medium to a final concentration of 100 nM to induce apoptosis. Total RNA extraction was by the RNeasy Total RNA Kit (Life Technologies) using reagents and instructions provided by the manufacturer. Reverse transcription of total RNA was performed with the reagents and instructions for gene-specific reverse transcription provided in the BRL Preamplification Kit (Life Technologies). Specifically, a 27 base 3' antisense oligonucleotide ("MORT1 downstream," 5'-TAG ATG CCT GTG GTC CAC CAG CGC AAA-3', complementary to bases 663 to 637 of the MORT1 coding sequence) was synthesized on an ABI oligosynthesizer. Reverse transcription of 1 μg total RNA was primed using this oligonucleotide.

PCR amplification of NTERA2 cDNA was performed using DNA Taq polymerase and other reagents provided by the manufacturer (Life Technologies) and equimolar amounts of oligonucleotides "5' MORT1" and "3' MORT1" (see above). Thermal cycling of the PCRs was in the Gene Amp 2400 thermal cycler (Perkin Elmer) under the regime, 1 min at 95C, 35 cycles (15 sec at 95C, 30 sec at 50C, 1 min at 72C), 7 min at 72C. The resulting PCR product (the cDNA corresponding to the MORT1Δ21 isoform) was agarose gel purified using Qiaex II reagents and instructions provided by the manufacturer (Qiagen) and ligated to the pCR2.1 cloning vector (Invitrogen). Recombinant plasmids were obtained by standard methodology, including transformation into One Shot *E. coli* cells (Invitrogen), growth of transformed bacterial cells on LB-agar plates containing 100 μg/mL ampicillin (Sigma), growth of bacterial colonies in LB Medium (Life Technologies,), and preparation of plasmid DNA using the QIAprep Spin Miniprep Kit (Qiagen). DNA sequence was obtained using cycle sequencing dideoxy terminator reagents (ABI) and synthetic oligonucleotides (see below) reacted in a Gene Amp 9600 thermal cycler (Perkin Elmer) under manufacturer's instructions. Reactions were run and data were generated on an ABI automated sequencer. Sequence data were analyzed using Lasergene software (DNA Star).

Oligonucleotides for use in DNA sequencing were prepared (on an ABI synthesizer), designed according to the sequence of the polylinker region of pCR2.1 and published MORT1 sequence. The following oligonucleotides were generated: "TA Forward" (5'-CAG GAA ACA GCT ATG ACC ATG-3', corresponding to the sense strand of the lacZ gene in pCR2.1, 67 bp upstream of the TA cloning site), "TA Reverse" (5'-ACG TTG TAA AAC GAC GGC CAG-3', corresponding to the antisense strand of the lacZ gene in pCR2.1, 112 bases downstream of the TA cloning site), "MORT 150" (5'-ACC TCT TCT CCA TGC TGC TG-3', sense strand, corresponding to bases 131 to 150 of the MORT1 coding sequence), "MORT 230" (5'-TCG AAG TCG TCG ACG CGC CG-3', antisense strand, complementary to bases 248 to 229 of the MORT1 coding sequence), "MORT 400" (5'-TCG ACA GCA TCG AGG ACA GA-3', sense strand, corresponding to bases 377 to 396 of the MORT1 coding sequence), and "MORT 420" (5'-GAT TCT CAG TGA CTC CCG CA-3', antisense strand, complementary to bases 441 to 422 of the MORT1 coding sequence).

Example 3
Cloning of MORT1 from NTERA2 Cells Using Nested Primers

NTERA2 cells (Stratagene) were grown under conditions to promote terminal differentiation to the neuronal phenotype, including long-term incubation in retinoic acid (Andrews, 1984). Eighteen hours prior to RNA extraction, staurosporine (Calbiochem) was added to the cell culture medium to a final concentration of 100 nM to induce apoptosis. Total RNA extraction was by the BRL RNeasy Total RNA Kit (Life Technologies, Inc.) using reagents and instructions provided by the manufacturer. Reverse transcription of total RNA was performed with the reagents and instructions provided in the BRL Preamplification Kit (Life Technologies, Inc.). Specifically, reverse transcription of 4 μg total RNA was primed using oligo(dT).

Oligonucleotides for use in PCR were prepared (on an ABI oligosynthesizer), designed according to the published MORT1 sequence (Genbank x84709). A 25 base 5' sense oligonucleotide ("MORT1 upstream," 5'-AAG CGG CGA GAC CTG GCC ACG GCC A-3', corresponding to bases −90 to −66, relative to the translational start site) was synthesized. PCR amplification of NTERA2 cDNA was performed using DNA Taq polymerase and other reagents provided by the manufacturer (Life Technologies) and equimolar amounts of "MORT1 upstream" and "MORT1 downstream" (see above) oligonucleotides. Thermal cycling of the PCRs was in the Gene Amp 2400 thermal cycler (Perkin Elmer, Inc.) under the regime, 1 min at 95C, 35 cycles (15 sec at 95C, 30 sec at 50C, 1 min at 72C), 7 min at 72C. A 2 μL aliquot of the 100 μL reaction served as the DNA template for further PCR amplification using equimolar amounts of oligonucleotides "5' MORT1" and "3' MORT1" (see above) under the same thermal cycling regime.

The resulting PCR product (the cDNA corresponding to the MORT1Δ21 isoform) was agarose gel purified using Qiaex II reagents and instructions provided by the manufacturer (Qiagen) and ligated into the pCR2.1 cloning vector (Invitrogen). Recombinant plasmids were obtained by standard methodology, including transformation into One Shot E. coli cells (Invitrogen), growth of transformed bacterial cells on LB-agar plates containing 100 μg/mL ampicillin (Sigma), growth of bacterial colonies in LB Medium (Life Technologies), and preparation of plasmid DNA using the QIAprep Spin Miniprep Kit (Qiagen). DNA sequence was obtained using cycle sequencing dideoxy terminator reagents (ABI) and synthetic oligonucleotides (see above) reacted in a Gene Amp 9600 thermal cycler (Perkin Elmer) under manufacturer's instructions. Reactions were run and data were generated on an ABI automated sequencer. Sequence data were analyzed using Lasergene software (DNA Star).

Example 4
Cloning of MORT1 Isoforms from Brain Tissue

The MORT1 cDNA from human fetal brain was generated using standard PCR techniques. Thermal cycling was performed, using the regime, 1 min at 95C, then 30 cycles (40 sec at 95C, 1 min at 60C, 1 min at 72C), 10 min at 72C, and using the oligonucleotides "5' MORT1" and "3' MORT1" (see above). A human fetal brain (matchmaker) cDNA library (Clontech) and a human adult whole brain (matchmaker) cDNA library (Clontech) were used as DNA templates for PCR. The PCR products of approximately 640 bp were obtained, ligated to the vector pCR II (Invitrogen), and recombinant plasmids were obtained by standard methodology, including transformation into competent One shot E. coli cells, growth of transformed bacterial cells on LB-agar plates containing 100 μg/mL ampicillin (Sigma), growth of bacterial colonies in LB Medium (Life Technologies), and preparation of plasmid DNA using by Wizard Plus Minipreps (Promega) or by Qiagen Midiprep (Qiagen). Recombinant plasmids were confirmed by restriction enzyme digestion. The cDNA sequence was determined by dye-deoxy terminator reaction using reagents and protocols from ABI-Perkin-Elmer and the ABI 373A automated sequencer.

The sequence of each of five clones isolated from human fetal brain cDNA matched the published MORT1 sequence. Five clones isolated from human adult brain cDNA were also sequenced. Three of five clones encoded the isoform that contained the deletion of bp 172–192 of the MORT1 coding sequence; the other two clones encoded a single base pair substitution (G173A) relative to the Genbank (X84709) MORT1 sequence.

Example 5
Cloning of MACHa1 from NTERA2 Cell cDNA

NTERA2 cells (Stratagene) were grown under conditions to promote terminal differentiation to the neuronal phenotype, including long-term incubation in retinoic acid (Andrews, 1984). Eighteen hours prior to RNA extraction, staurosporine (Calbiochem) was added to the cell culture medium to a final concentration of 100 nM to induce apoptosis. Total RNA extraction was by the BRL RNeasy Total RNA Kit (Life Technologies, Inc.) using reagents and instructions provided by the manufacturer. Reverse transcription of total RNA was performed with the reagents and instructions provided in the BRL Preamplification Kit (Life Technologies, Inc.). Specifically, reverse transcription of 4 μg total RNA was primed using oligo(dT).

Oligonucleotides for use in PCR were prepared (on an ABI oligosynthesizer), designed according to the published MACH sequence (Boldin, et al., 1996). A 24 base molecule (MACH 5'α, 5'-TTT-AAA-AAG-ATG-GAC-TTC-AGC-AGA-3', spanning the translational start codon of MACHα1 and other MACH isoforms) was synthesized. Another 24 base molecule (MACH 3'α, 5'-ATA-GCA-CCA-TCA-ATC-AGA-AGG-GAA-3', complementary to coding sequence, and spanning the stop codon of MACHα1 and MACHα2. PCR amplification of NTERA2 cDNA was performed using DNA Taq polymerase and other reagents provided by the manufacturer (Life Technologies) and equimolar amounts of oligonucleotides MACH 5'α and MACH 3'α (see above). Thermal cycling of the PCRs was in the Gene Amp 2400 thermal cycler (Perkin Elmer) under the regime, 1 min at 95C, 35 cycles (15 sec at 95C, 30 sec at 50C, 1 min at 72C), 7 min at 72C. Two PCR products, both between 1.4 and 1.5 kb resulted. The larger product (the cDNA corresponding to the MACHα1) was agarose gel purified using Qiaex II reagents and instructions provided by the manufacturer (Qiagen) and ligated to the pCR2.1 cloning vector (Invitrogen). Recombinant plasmids were obtained by standard methodology, including transformation into One Shot E. Coli cells (Invitrogen), growth of transformed bacterial cells on LB-agar plates containing 100 μg/mL ampicillin (Sigma), growth of bacterial colonies in LB Medium (Life Technologies,), and preparation of plasmid DNA using the QIAprep Spin Miniprep Kit (Qiagen). DNA sequence was obtained using cycle sequencing dideoxy terminator reagents (ABI) and synthetic oligonucleotides reacted in a Gene Amp 9600 thermal cycler (Perkin Elmer) under manufacturer's instructions. Reactions were run and data were generated on an ABI automated sequencer. Sequence data were analyzed using Lasergene software (DNA Star).

Example 6
Interaction of MORT1 Transcript Isoforms with MACHa1 C360S

To investigate the interaction of MORT1 transcript isoforms, a two-hybrid interaction paradigm was first established with MORT1 and MACHa1 C360S. Genes encoding the fusion proteins were generated by cloning MORT1 and MACHa1 C360S cDNA sequences into plasmids containing the coding regions for the domains of the yeast transcriptional activator proteins, Gal4. DNA binding domain (Gal4) fusion are constructed in pAS1 having a 2 m origin of replication which is described in Wade-Harper et al., (1993). Gene activation domain (Gal4) fusions are constructed in pACTII (described in Durfee et al., 1993). The yeast system used in this study is as described by Young and Ozenberger (1995).

The MORT1 cDNA is obtained as a Ncol-Bam HI fragment from MORT1-pCRII plasmid and directionally cloned into pAS1 via Ncol and BamHI restrictions sites to generate MORT1-pAS1 plasmid. The MACHa1 wildtype protein is lethal in yeast. Mutation of the cysteine at amino acid position 360 to a serine prevents the lethal phenotype and does not interfere with the protein's ability to interact with MORT1 (Boldin, et al., 1996). The amino acid substitution to generate MACHa1 C360S was obtained using standard PCR techniques (Finney, 1993). Thermal cycling of these reactions was performed under the regime, 1 min at 95C, then 30 cycles (40 sec at 95C, 1 min at 60C, 1 min at 72C), and 10 min at 72C, and using specific oligonucleotides. All oligonucleotides were prepared on an ABI oligosynthesizer and are designed according to published cDNA for human MACH (Boldin et al., 1996; Genbank X98172–X98178). Four oligonucleotides were prepared. A 36 base 5' mutagenic oligonucleotide (oCB1) contained the C360S substitution (TGT to TCT) and a silent mutations at Ala 359 (GCT to GCA) to encrypt a diagnostic restriction enzyme site for Sfil [5'-GTG TTT TTT ATT CAG GCA TCT CAG GGG GAT AAC TAC-3']. A 36 base 3' mutagenic oligonucleotide (oCB2) [5'-GTA GTT ATC CCC CTG AGA TGC CTG AAT AAA AAA CAC-3'] contained sequence complimentary to oCB1. A 34 base oligonucleotide (oCB3) containing a BamHI site [5'-CGG GAT CCG TAT GGA CTT CAG CAG AAA TCT TTA T-3']. A 38 base 3' oligonucleotide (oCB4) contained a BamHI and SalI restriction enzyme sites [5'-CGG GAT CCG ACG TCG ACT CAA TCA GAA GGG AAG ACA AG-3']. The MACHa1-pCR2.1 plasmid (see example 5, above) was used as template with oligonucleotide pair oCB2 and oCB3 to generate a 1100 basepair fragment, and as template for oligonucleotide pair oCB1 and oCB4 to generate a 360 bp fragment. A subsequent PCR reaction was performed using the 1100 and 360 basepair fragments with oligonucleotide pair oCB3 and oCB4 to generate a 1460 bp fragment which was ligated to pCRII vector (Invitrogen) to generate MACHa1 C360S-pCRII. Recombinant plasmids were obtained by standard methodology, including transformation into One Shot E. coli cells (Invitrogen), growth of transformed bacterial cells on LB-agar (Gibco, Inc.) plates containing either 100 mg/mL ampicillin (Sigma) or 50 mg/mL Kanamycin (Sigma) as described in the manufacturer's (Invitrogen) standard protocol. Growth of bacterial colonies was in LB medium and preparation of plasmid DNA was performed using Qiagen Midiprep (Qiagen) or Wizard Plus Minipreps (Promega). Recombinant plasmids were confirmed restriction enzyme digestion. The cDNA sequence was obtained by dye-deoxy terminator reactions using reagents and protocols from ABI-Perkin-Elmer and the ABI 373A automated sequencer. The cDNA encoding MACHa1 C360S was obtained as a BamHI-SalI fragment and directionally cloned into pACTII via BamHI-XhoI sites to generate MACHa1 C360S-pACTII. DNA of final recombinant vectors were transformed into yeast strain(s) by the lithium acetate method (Rose et al., 1990).

A yeast host strain (CY770) as described in Young and Ozenberger (1995) was transformed with both the MORT1 and MACHa1 C360S fusion constructs (YCB5) or a single fusion construct plus the opposing vector containing unrelated heterologous DNA (YCB5.1 or YCB2.1, respectively). All strains were found to exhibit equal growth on nonselective medium. Strains were then tested for growth on selective medium (i.e., growth medium lacking histidine). Only cells expressing both the MORT1 and MACHa1 C360S fusions are able to grow on selective medium while the strains containing either the MORT1 or the MACHa1 C360S fusion with an unrelated fusion cannot grow (data not shown).

The MORT1 G173A SEQ. (ID NO. 5) was obtained as a Ncol-BamHI fragment from MORT1 G173A-pCRII and directionally cloned into pAS1 to generate MORT1 G173A-pAS1 plasmid. MORT1Δ21 was obtained as a Ncol-BamHI fragment from MORT1Δ21-pCRII and directionally cloned into pAS1 to generated MORT1Δ21-pAS1 plasmid. These plasmids and the MACHa1 C360S-pACTII plasmid were used to transform the yeast host strain, CY770. Strains were generated that express MORT1 G173A and MACHa1 C360S fusion constructs (YCB16) or the MORT1 G173A fusion construct plus the opposing vector containing unrelated heterologous DNA (YCB16.1). Strains were generated that express MORT1Δ21 and MACHa1 C360S fusion constructs (YCB9) or the MORT1Δ21 fusion construct plus the opposing vector containing unrelated heterologous DNA (YCB9.1).

Figure 1:
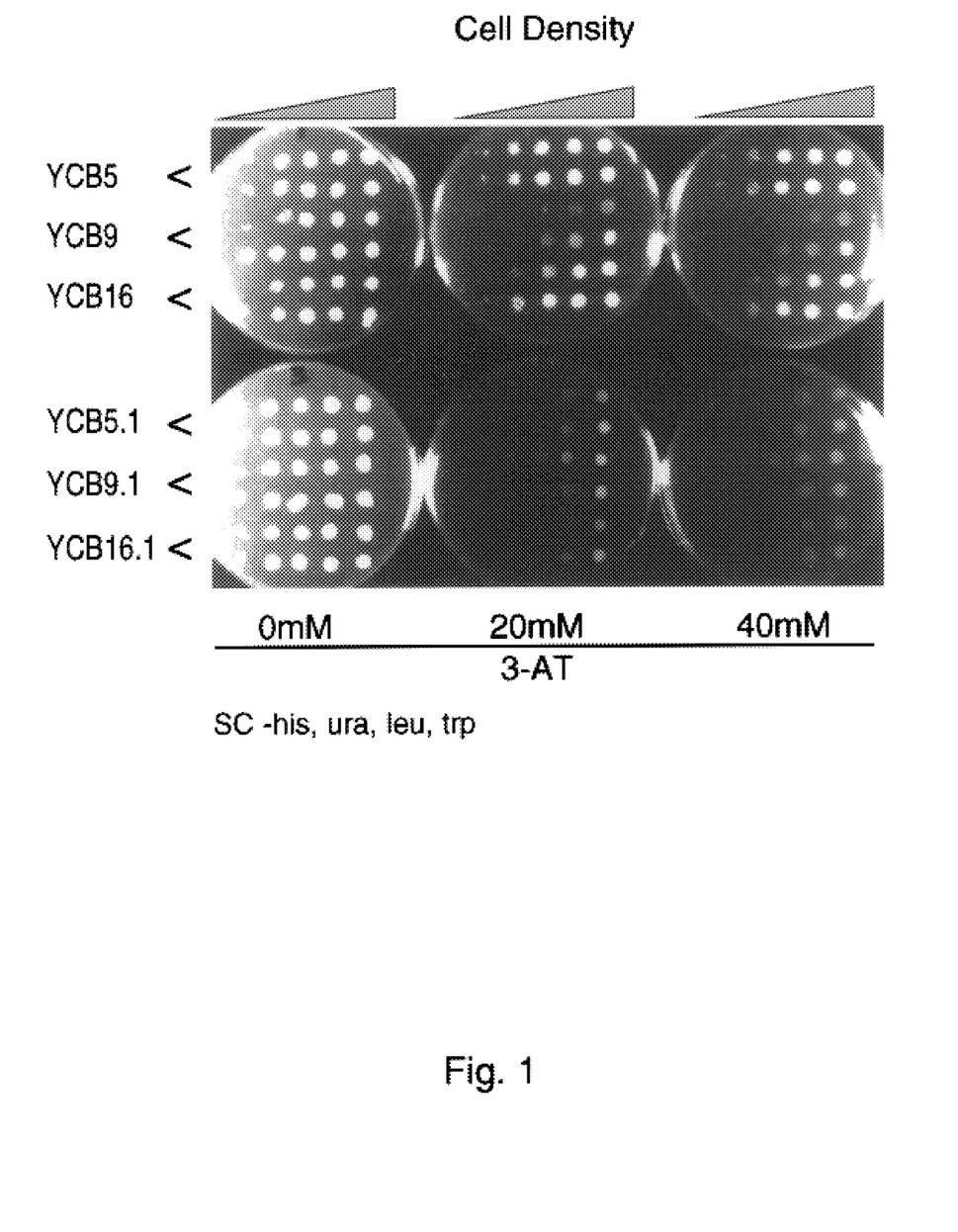
FIG. 1: Investigation of the MORT1 transcript isoforms with MACHα1 C360S in a yeast two-hybrid system: Activation of the HIS3 reporter gene. Each MORT1 transcript isoforms was expressed as a fusion protein with Gal4 DNA binding domain. MACHα1 C360S was expressed as a fusion protein with the Gal4 activation domain. Yeast strains were plated at a cell density of $5 \times 10^1$, $5 \times 10^2$, $5 \times 10^3$, $5 \times 10^4$ and $5 \times 10^5$ (left to right within a plate. Sibling isolates from yeast strains expressing a MORT1 transcript isoform with MACHα1 C360S fusion proteins were plated on histidine deficient media containing 0, 20 or 40 mM 3-aminotriazole (3-AT). The top row of plates (1) contained yeast strains that express two fusion proteins as follows: YCB5: MORT1-pAS1/MACHα1 C360S-pACTII; YCB9: MORT1Δ21-pAS1/MACHα1 C360S-pACTII; YCB16: MORT1 G173A-pAS1/MACHα1 C360S-pACTII. The bottom row of plates (3) contains negative control strains which express only the MORT1 transcript isoform fusion protein with a recombinant vector containing nonrelated heterologous DNA, as follows: YCB5.1: MORT1-pAS1/SNF4-pACTII; YCB9.1: MORT1 G173A/SNF4-pACTII; YCB16.1: MORT1Δ21-pAS1/SNF4-pACTII. Functional interaction of the MORT1 transcript isoform fusion protein with the MACHα1 C360S fusion protein reconstitutes the function of the Gal4 protein and drives HIS3 reporter gene activity thereby linking MORT1 isoform/MACHα1 C360S interaction to histidine prototrophy and yeast cell growth.
Figure 2:
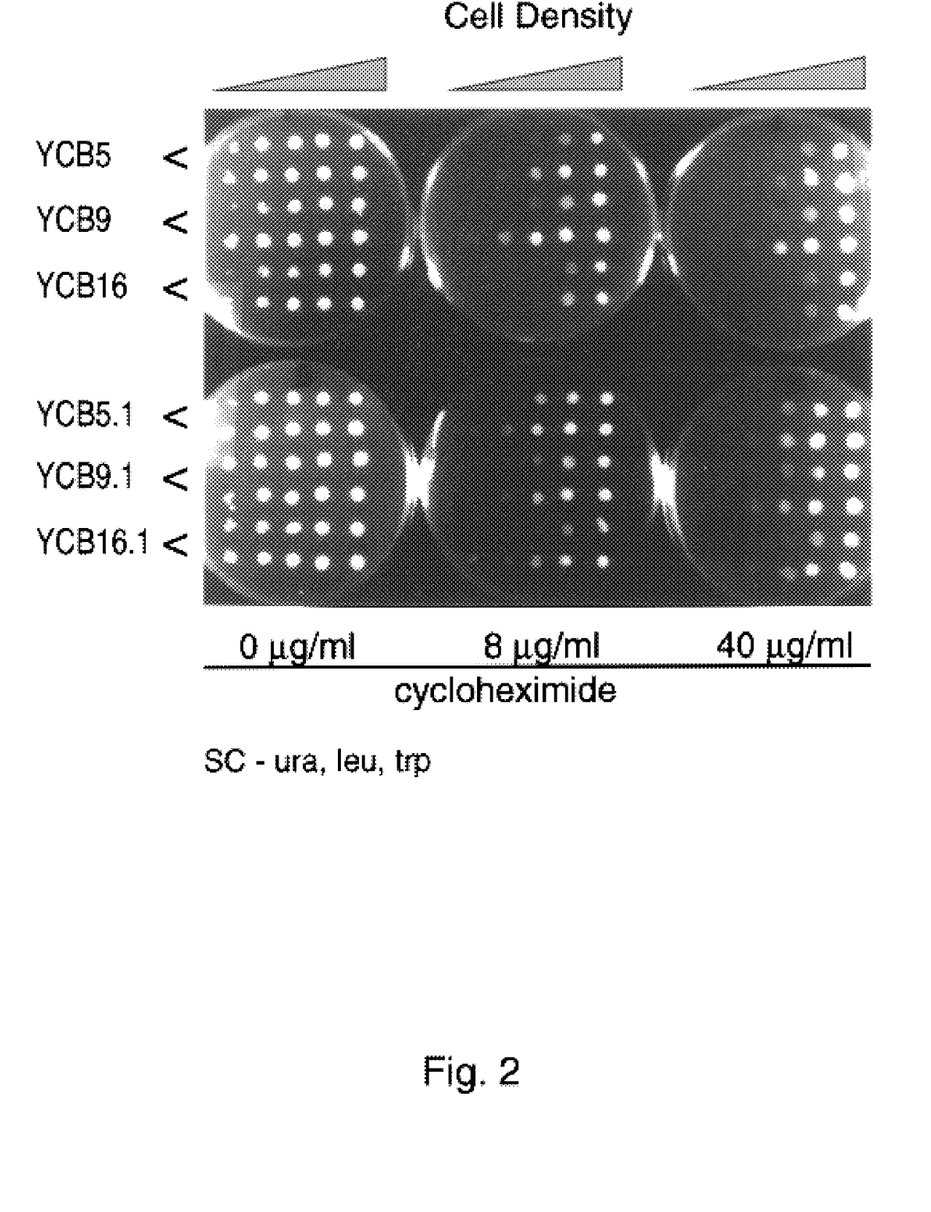
FIG. 2: Investigation of the MORT1 transcript isoforms with MACHα1 C360S in a yeast two-hybrid system: Activation of the CYH2 reporter gene. Each MORT1 transcript isoforms was expressed as a fusion protein with Gal4 DNA binding domain. MACHα1 C360S was expressed as a fusion protein with the Gal4 activation domain. Yeast strains were plated at a cell density of $5 \times 10^1$, $5 \times 10^2$, $5 \times 10^3$, $5 \times 10^4$ and $5 \times 10^5$ (left to right within a plate. Sibling isolates from yeast strains expressing a MORT1 transcript isoform with MACHα1 C360S fusion proteins were plated on selective media containing 0, 8 or 12 ug cycloheximide/mL media. The top row of plates (1) contained yeast strains that express two fusion proteins as follows: YCB5: MORT1-pAS1/MACHα1 C360S-pACTII; YCB9: MORT1Δ21-pAS1/MACHα1 C360S-pACTII; YCB16: MORT1 G173A-pAS1/MACHα1 C360S-pACTII. The bottom row of plates (3) contains negative control strains which express only the MORT1 transcript isoform fusion protein with a recombinant vector containing nonrelated heterologous DNA, as follows: YCB5.1: MORT1-pAS1/SNF4-pACTII; YCB9.1: MORT1 G173A/SNF4-pACTII; YCB16.1: MORT1Δ21-pAS1/SNF4-pACTII. Functional interaction of the MORT1 transcript isoform fusion protein with the MACHα1 C360S fusion protein reconstitutes the function of the Gal4 protein and drives CYH2 reporter gene activity thereby linking MORT1 isoform/MACHα1 C360S interaction to sensitivity to cycloheximide and abrogation of yeast cell growth.

Two independent samples of each strain were streaked on standard synthetic medium containing 0, 20 or 40 mM 3-aminotriazole (FIG. 2). Plates were incubated at 30C for 3 days. All strains were found to exhibit equal growth on non-selective medium. Strains were then tested for growth on selective medium (i.e., growth medium lacking histidine). Cells expressing both the MORT1 and MACHa1 C360S fusions, and cells expressing the MORT1 G173A isoform and MACHa1 C360S fusions, were able to grow on selective medium while the strains containing the MORT1Δ21 and MACHa1 C360S fusions were not able to grow (FIG. 2). Negative control stains expressing any of the MORT1 isoform fusions or the MACHa1 C360S fusion with an unrelated fusion cannot grow.

These data suggest that the MORT1Δ21 isoform fusion protein is impaired in its ability to functionally interact with the MACHa1 C360S fusion protein.

Example 7
Screen for Compounds Affecting the Interaction of MORT1 Transcript Isoforms with Other Interacting Proteins (MACH family members)

The screening methods as described in Young and Ozenberger, WO 95/34646 published Dec. 21, 1995, the whole of which is incorporated herein, are used to identify compounds that affect the interaction of MORT1 transcript isoforms with proteins such as MACHa1 C360S.

Low copy number plasmids expressing MORT1 transcript isoforms (MORT1 G173A or MORT1Δ21) and MACHa1 C360S as GAL4 fusion proteins are constructed to reduce expression of these proteins. cDNA inserts encoding the MORT1 transcript isoforms are subcloned directly from the recombinant pAS1 vector(s) to pUN30AS via Ncol-BamHI fragment to generate either MORT1 G173A-pUN30AS or MORT1 D 21-pUN30AS. The MACHa1 C360S is subcloned directly from the MACHa1 C360S-pCR II as a BamHI-Sal1 fragment into pUN100ACT via BamHI-Xhol sties to generate MACHa1 C360S-pUN100ACT. These plasmids are transformed into yeast strain CY770 (Young and Ozenberger, 1995) with reporter plasmid pOZ146 (Young and Ozenberger, 1995) to generate yeast strain YCB6. The presence of all three plasmids is necessary to confer the necessary phenotype to enable a rescue screen method as described in Young and Ozenberger (1995).

The yeast strain (YCB18) containing the MORT1 G173A and MACHa1 C360S fusion plasmids plus the reporter plasmid, or the yeast strain (YCB17) containing the MORTD21 and MACHa1 C360S plus the reporter plasmid, forms the basis of a simple primary screen for compounds that disrupt the interaction of the MORT1 transcript isoform gene products and MACHa1 C360S.

Example 8
Screen for Compounds Affecting the Interaction of MORT1 Transcript Isoforms and Protein Containing a Death Domain Motif (TRADD, Fas/APO1 Receptor, TNFR)

The screening methods as described in Young and Ozenberger, WO 95/34646 published Dec. 21, 1995, the whole of which is incorporated herein, are used to identify compounds that affect the interaction of MORT1 transcript isoforms with proteins containing a death domain motif.

Low copy number plasmids expressing MORT1 transcript isoforms (MORT1 G173A, or MORT1Δ21) and the cytoplasmic domain of the TNF receptor containing a death domain motif as GAL4 fusion proteins are constructed to reduce expression of these proteins. cDNA inserts encoding the MORT1 transcript isoforms are subcloned directly from the MORT1 G173A-pAS1 or the MORT1Δ21-pAS1 recombinant to pUN30AS via Ncol-BamHI fragment to generate either MORT1 G173A-pUN30AS or MORT1Δ21-pUN30AS. The cytoplasmic domain of the TNFR is subcloned directly from TNFcyto-pCR II as an EcoRI fragment into pUN100ACT via EcoRI sites to generate TNFRcyto-pUN100ACT. Plasmids are transformed into the yeast strain CY770 (Young and Ozenberger, 1995) with the reporter plasmid pOZ146 (Young and Ozenberger, 1995). The presence of three plasmids is necessary to confer the necessary phenotype to enable a rescue screen method as described in Young and Ozenberger (1995). The yeast strain (YCB21) containing the MORT1 G173A and TNFRcyto fusion plasmids plus the reporter plasmid, or the yeast strain (YCB20) containing the MORT1Δ21 and TNFRcyto plus the reporter plasmid, forms the basis of a simple primary screen for compounds that disrupt the interaction of the MORT1 transcript isoform gene products and a death domain containing protein, TNFR cytoplasmic domain.

REFERENCES

Andrews P W. (1984) Retinoic acid induces neuronal differentiation of a cloned human embryonal carcinoma cell line. In Vitro Dev Biol 103: 285–293

Ausubel F M, Brent R., Kingston R E, Moore D D, Seidman J G, Smith J and Struhl K (eds.). (1993) Current Protocols in Molecular Biology, Vol 2. John Wiley & Sons, New York Berk A J, Sharp P A. (1977) Sizing and mapping of early adenovirus mRNAs by gel electrophoresis of S1 endonuclease-digested hybrids. Cell 12: 721–732

Boldin M P, Varfolomeev E E, Pancer Z, Mett I L, Camonis J H, Wallach D. (1995) A novel protein that interacts with the death domain of Fas/APO1 contains a sequence motif related to the death domain. J Biol Chem 270: 7795–7798

Boldin M P, Goncharov T M, Goltsev Y V, Wallace D. (1996) Involvement of MACH, a novel MORT1/FADD-interacting protease, in Fas/Apo1- and TNF receptor induced cell death. Cell 85: 803–815

Chinnaiyan A M, O'Rourke K, Tewari M, Dixit V M. (1995) FADD, a novel death domain-containing protein, interacts with the death domain of Fas and initiates apoptosis. Cell 81: 505–512

Cordell H J, Todd J A, Bennett S T, Kawaguchi Y, Farrall M. (1995) Two-locus maximum lod score analysis of a multifactorial trait: joint consideration of IDDM2 and IDDM4 with IDDM1 in type 1 diabetes. Am J Hum Genet 57: 920–934

Coico R (ed.). (1994) Current Protocols in Immunology. John Wiley & Sons, New York Davies J L, Kawaguchi Y, Bennett S T, Copeman J B, Cordell H J, Pritchard L E, Reed P W, Gough S C, Jenkins S C, Palmer S M, et al. (1994) A genome-wide search for human type 1 diabetes susceptibility genes. Nature 371: 130–136

Durfee T, Becherer K, Chen P-L, Yeh S-H, Yang Y, Kilburn A E, Lee W-H, Elledge S J. (1993) The retinablastoma protein associated with the protein phosphatase type 1 catalytic sub-unit. Genes and Devel. 7: 555–569

Farrow S M. (1997) Basis of gene structure and function. In: Rumsby G and Farrow M (eds.), Molecular Endocrinology. BIOS Scientific Publishers, Ltd, Oxford, pp 1–22

Finney M. (1993) The polymerase chain reaction. In: Ausubel F M, Brent R, Kingston R E, Moore D D, Seidman J G, Smith J and Struhl K (eds.), Current Protocols in Molecular Biology, Vol 2. John Wiley & Sons, New York, Chapter 15

Fisher G H, Rosenberg F J, Straus S E, Dale J K, Middleton L A, Lin A Y, Strober W, Lenardo M J, Puck J M. (1995) Dominant interfering Fas gene mutations impair apoptosis in a human autoimmune lymphoproliferative syndrome. Cell 81: 935–946

Freshney R I. (1987) Culture of Animal Cells. A R Liss, New York

Glover D N (ed.). (1985) DNA Cloning, Vol 1 and 2. IRL Press, Oxford

Griffin H G, Griffin A M (eds.). (1994) PCR Technology: Current Innovations. CRC Press, Boca Raton, Fla.

Hanes B D, Higgins S J. (eds.) (1984) Transcription and Translation. IRL Press, Oxford Hashimoto L, Habita C, Beressi J P, Delepine M, Besse C, Cambon-Thomsen A, Deschamps I, Rotter J I, Djoulah S, James M R, et al. (1994) Genetic mapping of a susceptibility locus for insulin-dependent diabetes mellitus on chromosome 11q. Nature 371: 161–164

Henkart, P A. (1996) ICE family proteases: mediators of all apoptotic cell death? Immunity 4: 195–201

Kim P K M, Dutra A S, Chandrasekharappa S C, Puck J M. (1996) Genomic structure and mapping of human FADD, an intracellular mediator of lymphocyte apoptosis. J Immunol 157: 5461–5466.

Kischkel F C, Hellbardt S, Behrmann I, Germer M, Pawlita M, Krammer P H, Peter M E. (1995) Cytotoxicity-dependent APO-1 (Fas/CD95)-associated proteins form a death-inducing signaling complex (DISC) with the receptor. EMBO J 14: 5579–5588

Lafage M, Pedeutour F, Marchetto S, Simonetti J, Prosperi M T, Gaudray P, Birnbaum D. (1992) Fusion and amplification of two originally non-syntenic chromosomal regions in a mammary carcinoma cell line. Genes Chromosomes Cancer 5: 40–49

Lee J J, Costlow N A. (1987) A molecular titration assay to measure transcript prevalence levels. Methods Enzymol 152: 633–648

Lewin B. (1994) Genes V. Oxford University and Cell Press, Oxford.

Nagata S. (1994) Fas and Fas ligand: a death factor and its receptor. Adv Immunol 57: 129–144

Perbal B. (1988) A Practical Guide to Molecular Cloning, 2nd ed. John Wiley & Sons, New York Rieux-Laucat F, Le Deist F, Hivroz C, Roberts I A, Debatin K M, Fischer A, de Villartay J P. (1995) Mutations in Fas associated with human lymphoproliferative syndrome and autoimmunity. Science 268: 1347–1349

Rose, M D, Winston, F, Hieter, P. (1990) Methods in yeast genetics. Cold Spring Harbor Laboratory Press, Cold Spring Harbor, N.Y.

Sambrook J, Fritsch E F, Maniatis T. (1989) Molecular Cloning: A Laboratory Manual, Second Edition. Cold Spring Harbor Laboratory, Cold Spring Harbor, N.Y.

Schuuring E. (1995) The involvement of the chromosome 11q13 region in human malignancies: cyclin D1 and EMS1 are two new candidate oncogenes—a review. Gene 159: 83–96

Schuuring E, Verhoeven E, van Tinteren H, Peterse J L, Nunnink B, Thunnissen F B, Devilee P, Cornelisse C J, van de Vijver M J, Mooi W J, et al. (1992) Amplification of genes within the chromosome 11q13 region is indicative of poor prognosis in patients with operable breast cancer. Cancer Res 52: 5229–5234

Szepetowski P, Perucca-Lostanlen D, Grosgeorge J, LePaslier D, Brownstein B H, Carle G F, Gaudray P. (1995) Description of a 700-kb yeast artificial chromosome contig containing the BCL1 translocation breakpoint region at 11q13. Cytogenet Cell Genet 69: 101–107

Thompson C B. (1995) Apoptosis in the pathogenesis and treatment of disease. Science 267: 1456–1462

Tisch R, McDevitt H. (1996) Insulin-dependent diabetes mellitus. Cell 85: 291–297

Wade-Harper J, Adami G R, Wei N, Keyomarsk K, Elledge S J. (1993) The p21 Cdk-interacting protein Cip1 is a potent inhibitor of G1 cylcin-dependent kinases. Cell 75: 801–816

Young, K H, Ozenberger, B A. (1995) Novel cell systems having specific interaction of peptide binding pairs. WO 95/34646. December 21.

What is claimed is:

1. An isolated MORT1 isoform nucleotide sequence as set forth in SEQ. ID NO. 1.

2. An isolated MORT1 isoform nucleotide sequence as set forth in SEQ. ID NO. 3.

3. An isolated MORT1 isoform nucleotide sequence as set forth in SEQ. ID NO. 5.

* * * * *